United States Patent [19]

Gordon

[11] Patent Number: 4,606,644
[45] Date of Patent: Aug. 19, 1986

[54] GAS MEASURING APPARATUS WITH MEANS TO REDUCE THERMAL RADIATION EFFECTS

[75] Inventor: Daniel A. Gordon, San Jose, Calif.

[73] Assignee: Measurex Corporation, Cupertino, Calif.

[21] Appl. No.: 755,222

[22] Filed: Jul. 15, 1985

Related U.S. Application Data

[63] Continuation of Ser. No. 513,189, Jul. 12, 1983, abandoned.

[51] Int. Cl.[4] .............................................. G01N 21/00
[52] U.S. Cl. .................................. 356/438; 356/436; 356/437; 356/439
[58] Field of Search ................................. 356/436–439

[56] References Cited

U.S. PATENT DOCUMENTS

| | | | |
|---|---|---|---|
| 3,323,409 | 6/1967 | Fruengel | 356/437 X |
| 3,856,404 | 12/1974 | Hershler | 356/437 X |
| 4,420,687 | 12/1983 | Martinez | 356/437 X |

FOREIGN PATENT DOCUMENTS

| | | | |
|---|---|---|---|
| 0064200 | 11/1982 | European Pat. Off. | 356/437 X |
| 2849379 | 5/1979 | Fed. Rep. of Germany | 356/437 X |

Primary Examiner—Bernard D. Pianalto
Attorney, Agent, or Firm—Hal J. Bohner

[57] ABSTRACT

A gas measuring device has a source capable of emitting a beam of radiation aligned to impinge a detector. A housing means encloses the beam. The housing means has a plurality of apertures permitting the gas to enter the housing means, to intercept the beam, and to exit from the housing means. The device further comprises means to control the amount of thermal radiation reaching the detector.

6 Claims, 10 Drawing Figures

GAS MEASURING APPARATUS WITH MEANS TO REDUCE THERMAL RADIATION EFFECTS

This application is a continuation of application Ser. No. 513,189 filed July 12, 1983 now abandoned.

BACKGROUND OF THE INVENTION

1. Field of the Invention

The present invention relates to an apparatus for measuring the concentration of a gas. Typically, the gas is an exhaust gas, emitted through a stack, produced as a result of combustion.

2. Prior Art

Gas measuring apparatus for monitoring the output of combustion at a stack is well known. For example, one such system is taught in U.S. patent application Ser. No. 422,054 filed Sept. 23, 1982.

Typically such devices operate in a high temperature environment. If the temperature is sufficiently high, various parts of the system can generate electromagnetic radiation in the infrared, visible and ultraviolet ranges called thermal radiation, which can interfere with the system operation.

OBJECTS OF THE INVENTION

An object of the present invention is to provide a system for monitoring a gas in the presence of thermal radiation.

Further objects and advantages of the invention can be ascertained by reference to the specification and drawings herein which are by way of example only and not in limitation of the invention which is defined by the claims.

DETAILED DESCRIPTION OF THE DRAWINGS

Figure 1:
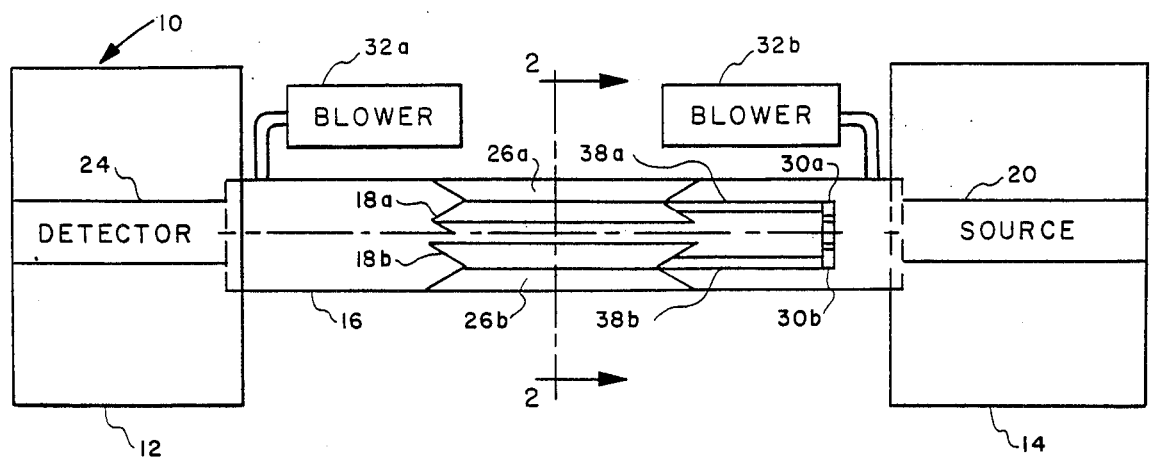
FIG. 1 is a side view of the gas measuring apparatus of the present embodiment.
Figure 2:
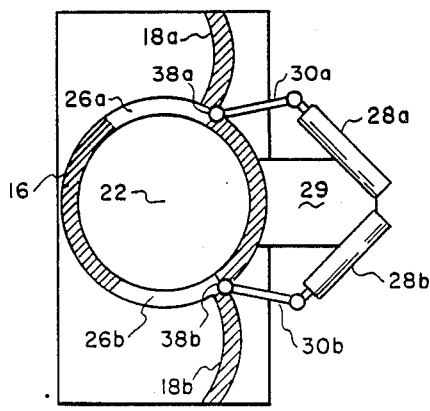
FIG. 2 is a cross-sectional view of FIG. 1 taken along the plane 2—2, showing the system in a particular operating mode.

Referring to FIG. 1 there is shown a gas measuring apparatus 10 of a preferred embodiment present invention. The gas measuring apparatus 10 comprises a first enclosure 12, and a second enclosure 14 each coupled to a hollow tube 16. The first enclosure 12 is to one side of the tube 16 while the second enclosure 14 is to the other side of the tube 16. A source system 20 is in the second enclosure 14. The source system 20 is capable of emitting a beam 22 of radiation (shown as dash-dot-dash line). The beam 22 is aligned to pass through the tube 16 and to impinge a detector system 24 in the first enclosure 12.

Figure 3:
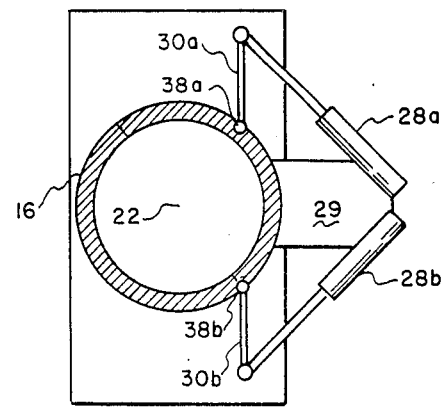
FIG. 3 is a cross-sectional view of FIG. 1 taken along the plane 2—2, showing the system in another operating mode.

The tube 16 has a plurality of apertures. The apertures 26a and 26b are located on opposite sides of the tube 16; they permit gas to enter the tube 16 via one aperture, e.g. 26b, to intercept the beam 22, and to exit via another aperture, e.g. 26a. A plurality of doors 18a and 18b are positioned to close each of the apertures of the tube 16. Each of the doors is hinged on a hinge 38a and 38b near each of the apertures 26a and 26b and is capable of pivoting about the hinge to close the aperture. A member, (e.g. 30a) is pivotably connected, at one end, to each hinge (e.g. 38a). A pneumatic actuator (e.g. 28a) is pivotably connected to each member (e.g. 30a) at the other end of each member (e.g. 30a). Each pneumatic actuator 28a and 28b is mounted on stand 29 connected to tube 16. The actuation by the pneumatic actuator 28a would close the aperture 26a, as shown in FIG. 3. Blowers 32a and 32b are provided to purge the gas from the inside of the tube 16.

Figure 4:
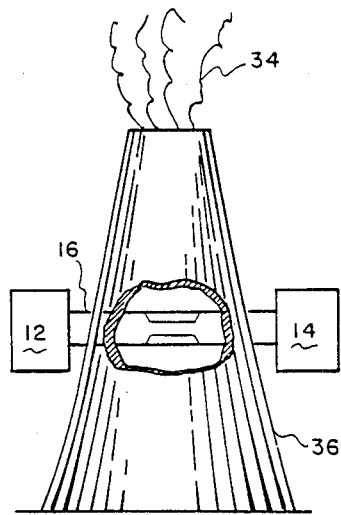
FIG. 4 is a pictorial view of the use of the apparatus of the present invention in a stack to monitor the exhaust gas from the combustion.

One use of the apparatus 10 of the present invention is in monitoring the exhaust gas 34 of combustion from a stack 36, shown in FIG. 4. Typically, the first enclosure 12 and the second enclosure 14 are on opposite sides of the stack 36, with the tube 16 passing through the stack 36. The information from the apparatus 10 can be used to control the combustion process.

Figure 6:
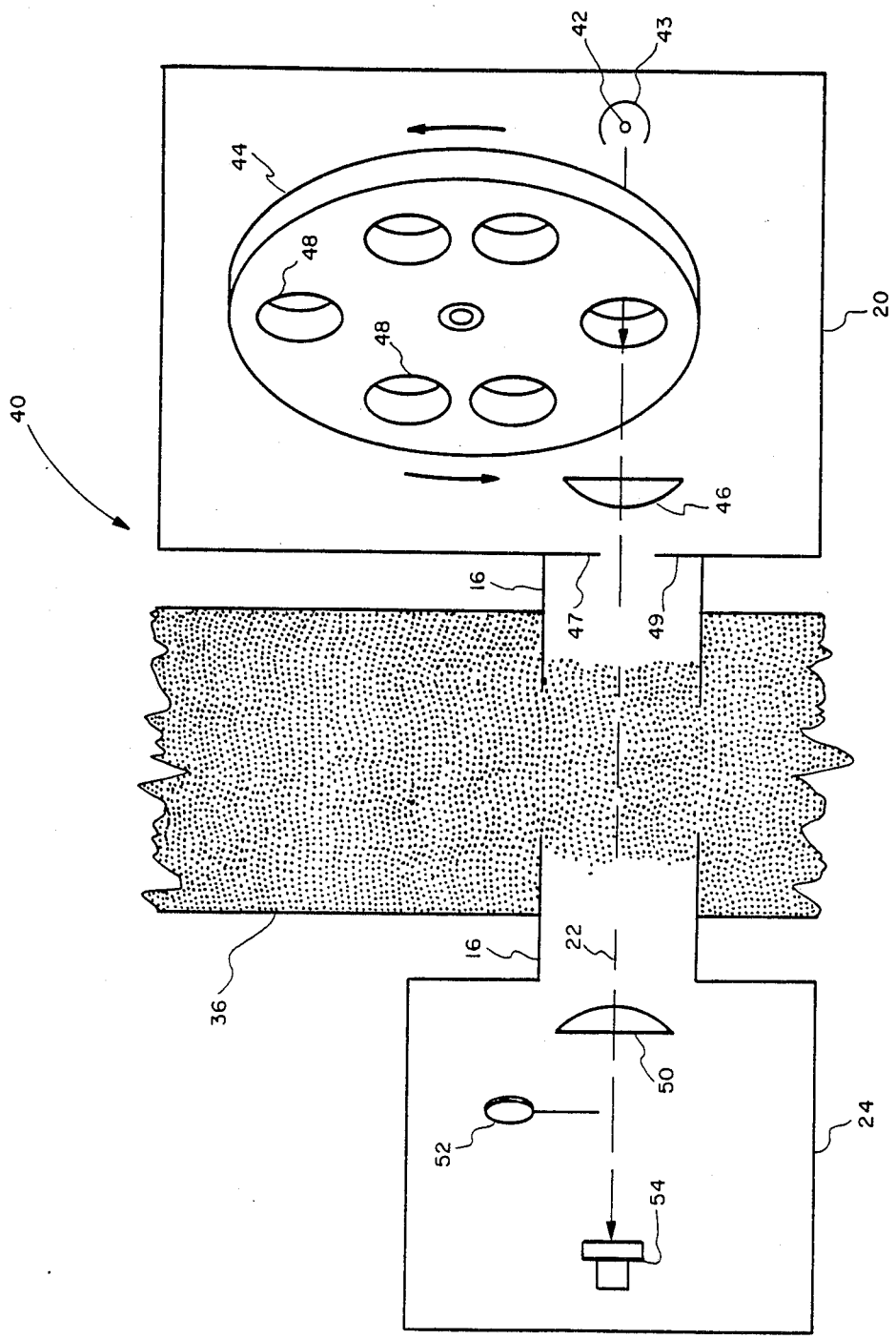
FIG. 6 is a detailed, cross-sectional view of the present apparatus.

Turning to FIG. 6, components of the source system 20 and detector system 24, which together comprise an optical system 40 are shown. The source system 20 includes a light source including a glowbar 42, a filter wheel 44, a collimating lens 46 and a port 47 formed in a wall 49. The glowbar 42 is in a housing 43 and is a ceramic rod which can be electrically heated so that it produces electromatic radiation, primarily in the infrared region. The filter wheel 44 is disc shaped and has a plurality of circular ports 48. Depending upon the gas to be measured by the optical system 40, some or all of the ports 48 contain filters, not shown, which can be solid or can have gas standards inside. The filter wheel is opaque and is rotatable about its central axis by a drive system, not shown. Thus when the filter wheel 44 rotates, light is intermittently obstructed by the wheel itself or permitted to pass through a cell in one of the ports 48; that is, the light is "chopped" at a frequency dependent upon the rate of rotation of the filter wheel 44.

After leaving the lens the chopped and filtered light travels through the gas in the stack 36 and thereafter into the detector system 12. The detector system 12 includes a lens 50, a standard cell 52 and a detector 54. A digital computer, not shown, is coupled to receive signals from the detector 54, and the computer is connected to the filter wheel 44 to receive signals indicative of the rate of rotation of the wheel 44. Thus, the wheel 44 chops light from the glowbar 42 at a predetermined phase and frequency thereby permitting the computer to distinguish light produced by the glowbar 42 from stray, unchopped light from other sources.

Figure 5:
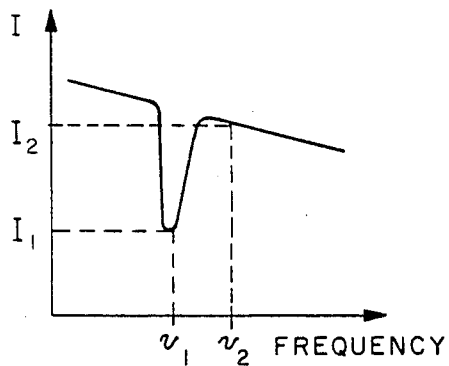
FIG. 5 is a graph of the absorption spectrum of a typical gas as a function of the frequency.

To operate the apparatus of the present invention, the glowbar 42 emits a beam 22 of radiation, and the filters in the filter wheel 44 are selected so that they pass light at a frequency shown as $v_1$ in FIG. 5 which is absorbed by the gas 34 and a frequency $v_2$, which is not. The chopped beam 22 passes through the gas 34 in the tube 16 and frequency $v_1$ is absorbed as it travels to the detector 24. The intensity of the light having frequency $\nu_1$ received by the detector 24 is dependent upon the amount of absorption, i.e. the greater the absorption, the lower the intensity of the beam 22 received by the detector 24, and vice versa. This is shown as $I_1$ in FIG. 5. The intensity of light having frequency $\nu_2$, $I_2$, is not dependent upon the amount of absorption. The concentration of gas 34 in the tube 16 is calculated based upon $I_1$ and $I_2$ in accordance with an experimentally determined calibration curve.

Often the gas temperatures in the stack 36 reach or exceed 500 degrees F. At such temperatures parts of the present system such as the tube 16 generate significant amounts of thermal radiation, which is electromagnetic radiation having a wide range of frequencies. I have found that in some circumstances the thermal radiation can enter the source system in a device lacking my invention and impinge upon the filter wheel 44 and be chopped and reflected to the detector 54. Chopped thermal radiation which reaches the lens 50 and has the same frequency as is generated by the glowbar 42 is indistinguishable from chopped light from the glowbar. Thus when significant amounts of such thermal radiation are received by the detector 54 the calibration of the system can be upset.

Figure 8:
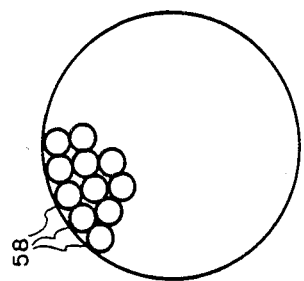
FIG. 8 is a view of FIG. 7 taken along section 8—8.
Figure 10:
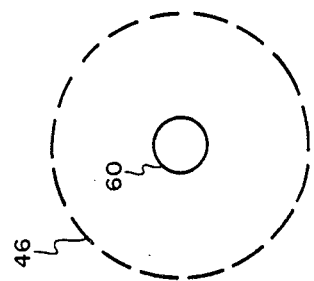
FIG. 10 is a view of FIG. 9 taken along section 10—10.
Figure 7:
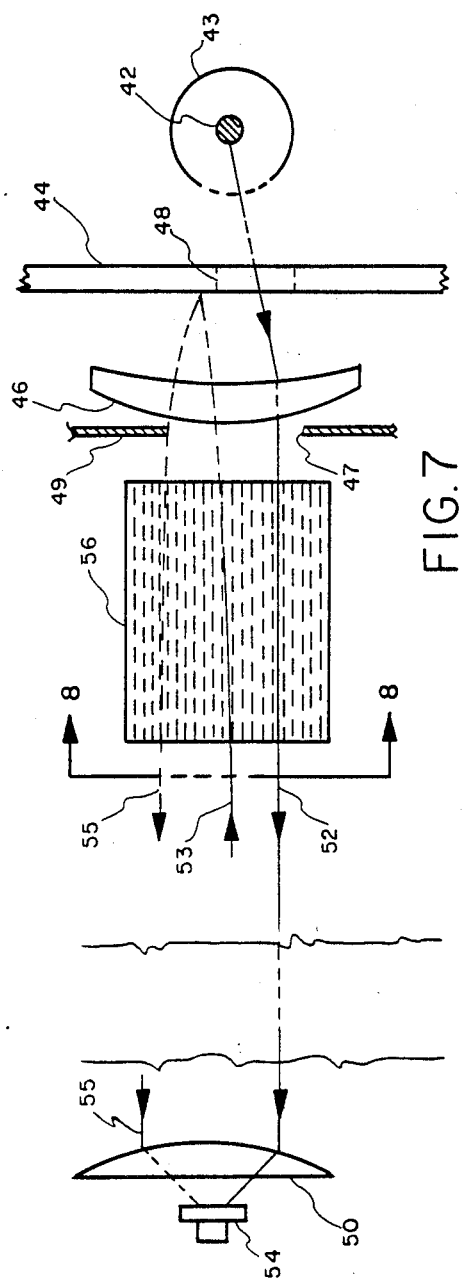
FIG. 7 is a detailed view of one part of one embodiment of the present apparatus.

Turning to FIGS. 7-10 there are shown embodiments of my solution to this problem. In FIG. 7 there is shown a collimator 56 positioned immediately to the left of port 47. As shown in FIG. 8, the collimator 56 is a cylindrical bundle of small tubes 58 which are glued to one another. Preferably the tubes are made of glass capillaries.

Thermal radiation generated in the tube 16 can impinge upon the collimator 50 from a wide range of angles. When a ray of thermal radiation enters one of the tubes 58 at greater than a predetermined angle, the ray is prevented from reaching the lens 46 as shown in FIG. 7. The lens 46 is a collimating lens so that a ray of light from its focal point, to the right of the lens, leaves the lens parallel to the axis of the lens. In the present apparatus the glowbar 42 is located at the focal point of the lens 46, and the axis of the lens coincides with the axis of the tube 16 and the axis of lens 50. Thus light from the glowbar 42 travels through the tube 16 in rays which are parallel to the axis of the tube. This is illustrated for example by ray 52.

On the other hand, the filter wheel 44 is not located at the focal point of the lens 46. Therefore, if the collimator 56 were not present, thermal radiation traveling from left to right and not parallel to the axis of the tube 16 could pass through the lens 46, be reflected from the filter wheel 44 and be converted by the lens 46 to rays traveling left and parallel to the axis of the tube 16. One such a hypothetical ray is identified as ray 53 as it travels right and ray 55 as it travels left. However, if the ray 53 were parallel to the axis of the tube 16, the collimating lens 46 would convert it to a ray 55 not parallel to the axis of the tube 16. Since the distance between lens 46 and lens 50 is large, only rays 55 which are parallel to the axis of tube 16 can reach the detector 54. Thus the collimator 56 prevents any signficant quantity of chopped thermal radiation from reaching the detector 54.

Figure 9:
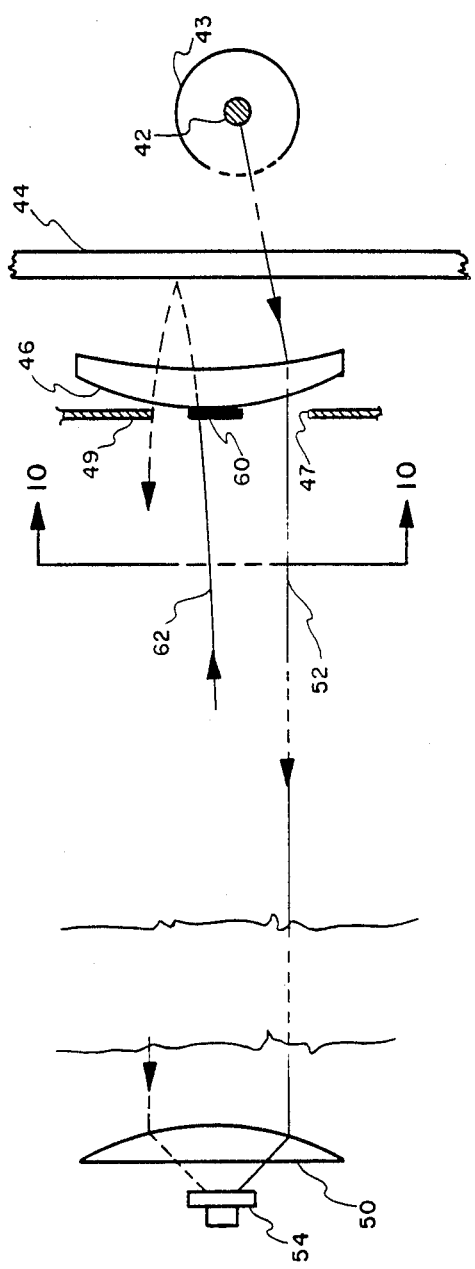
FIG. 9 is a detailed view of another embodiment.

Another embodiment is shown in FIG. 9 and includes an opaque blocking spot 60 affixed to the lens 46. I have found that by making the blocking spot 60 sufficiently large in diameter, thermal radiation, such as ray 62, is prevented from reaching the filter wheel 44. However, the spot 60 should not be so large that significant amounts of light from the glowbar are obstructed. Preferably the size of the spot 60 should be related to the size of the port 47 so that no significant quantity of thermal radiation reaches the lens 50. In practice, I have found that for a one inch diameter port 47, the spot 60 should be about nine sixteenths inch in diameter.

I claim:

1. A system for monitoring a gas in the presence of thermal radiation comprising:
   (a) an optical system including a first source of a beam of radiation and a detector to receive the beam, said optical system being constructed so that the beam of radiation passes through the monitored gas;
   (b) chopper means located between said first source and said detector and coupled to the optical system to chop the beam;
   (c) a collimating lens located between said chopper means and said detector; and
   (d) radiation control means coupled to the optical system to prevent thermal radiation, which is generated by a second source of radiation located to the side of said lens opposite said first source, from traveling through said lens, thereafter reflecting from said chopper means, and thereafter being collimated by said collimating lens and impinging on said detector.

2. A system according to claim 1 wherein the optical system includes a slotted, purgable pipe.

3. A system according to claim 1 wherein the gas is flowing through a stack, and the slotted, purgable pipe is mounted in said stack.

4. A system according to claim 1 wherein radiation control means includes a collimator located between said lens and said detector.

5. A system according to claim 1 wherein said radiation control means includes spot mounted on said lens.

6. A system according to claim 5 wherein the radiation control means further includes a port.

* * * * *

UNITED STATES PATENT AND TRADEMARK OFFICE
CERTIFICATE OF CORRECTION

PATENT NO. : 4,606,644

DATED : August 19, 1986

INVENTOR(S) : Daniel A. Gordon

It is certified that error appears in the above—identified patent and that said Letters Patent is hereby corrected as shown below:

```
Column 4, line 51 after "control means includes"
please add -- a blocking --.
```

Signed and Sealed this

Twenty-second Day of March, 1988

Attest:

DONALD J. QUIGG

*Attesting Officer*     Commissioner of Patents and Trademarks